(12) United States Patent
Mythen

(10) Patent No.: US 7,931,913 B2
(45) Date of Patent: *Apr. 26, 2011

(54) TONGUE CLEANING DEVICE WITH DISSOLVABLE BLISTER

(76) Inventor: Daniel Richard Mythen, Redmond, WA (US)

( * ) Notice: Subject to any disclaimer, the term of this patent is extended or adjusted under 35 U.S.C. 154(b) by 1216 days.

This patent is subject to a terminal disclaimer.

(21) Appl. No.: 11/553,620

(22) Filed: Oct. 27, 2006

(65) Prior Publication Data

US 2007/0049956 A1 Mar. 1, 2007

Related U.S. Application Data

(63) Continuation-in-part of application No. 11/093,785, filed on Mar. 29, 2005, now Pat. No. 7,592,018.

(51) Int. Cl.
*A61K 9/68* (2006.01)

(52) U.S. Cl. ...................................................... 424/440

(58) Field of Classification Search .................. None
See application file for complete search history.

(56) References Cited

U.S. PATENT DOCUMENTS 4,432,114 A * 2/1984 Goudsmit .................. 15/104.93

OTHER PUBLICATIONS

Notice of Allowance and Fee(s) Due dated Jun. 10, 2009 in U.S. Appl. No. 11/093,785.

* cited by examiner

*Primary Examiner* — Carlos A Azpuru
(74) *Attorney, Agent, or Firm* — Dergosits & Noah LLP

(57) ABSTRACT

A device for cleaning the tongue and mouth is formed to have beneficial surface features. Depressions are formed on one surface of the device to facilitate adhering the device to the roof of the mouth. Dissolvable blisters are formed on one surface to contain and deliver a material, such as mouthwash or medicine, into the mouth of the user. The blisters may formed with different wall thicknesses to provide a time-controlled release of the deliverable material.

20 Claims, 2 Drawing Sheets

FIG 1a
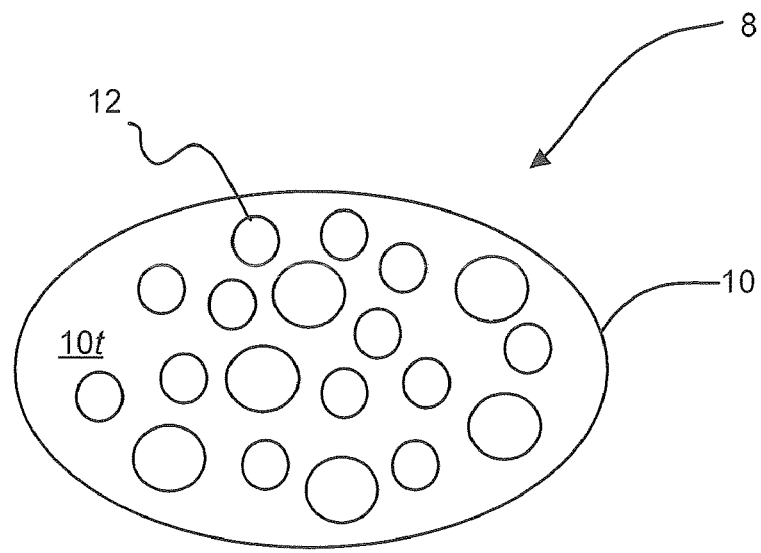
FIG 1b
FIG 1c
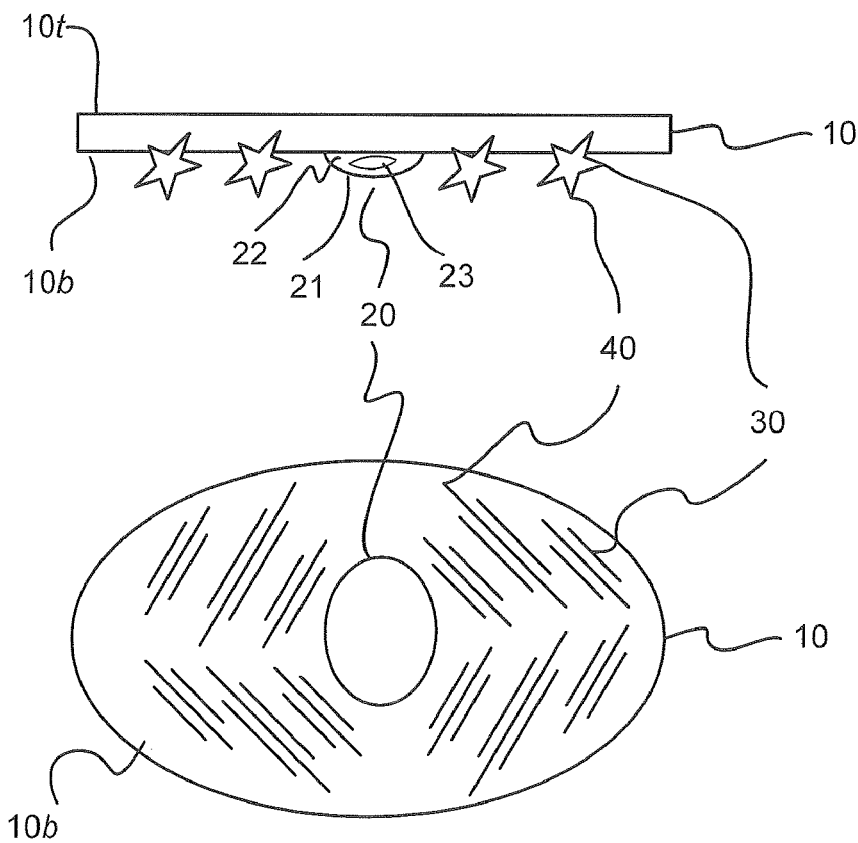

TONGUE CLEANING DEVICE WITH DISSOLVABLE BLISTER

BACKGROUND

The present disclosure relates to devices for cleaning the tongue and mouth.

Oral malodor, also known as bad breath or halitosis, is a common condition afflicting many people. The origin of oral malodor may be physiological or pathological in nature. However, even for individuals having healthy periodontal tissues and practicing good oral hygiene, the back of the tongue is a significant source of oral malodor due to the production of volatile sulfur compounds.

Various devices are known for addressing oral malodor. For example, U.S. Pat. No. 5,226,197 discloses a tongue hygiene device shaped like a toothbrush but with a wider than normal head, short bristles and a scraper. U.S. Pat. No. 6,004,334 discloses an edible confection having a soft side and a hard side, wherein the hard side has a raised pattern to help scrape the tongue. However, it remains desirable to find useful solutions that help to fight oral malodor.

SUMMARY

A device is formed to provide effective cleaning and tongue-scraping action, and/or to deliver modest amounts of a material, such as mouthwash or medicine. The device is preferably a soft pliable edible dissolvable confection formed to have beneficial surface features. One feature is a plurality of depressions formed on one surface of the device to facilitate adhering the device to the roof of the mouth. Another feature is a plurality of hard candy segments formed on a surface of the device. Preferably, the segments have raised ridges which are suitable for abrading the tongue. Another feature is at least one dissolvable blister formed on a surface to deliver a material.

In use, the device is adhered to the roof of the mouth and the user's tongue passes over the hard candy segments formed in the soft candy. Preferably, the soft candy is repeatedly removed and adhered in a new spot to permit more thorough coverage of the tongue until the candy is dissolved. Further, the blisters dissolve to deliver a material to the user's tongue. Advantageously, the blisters may have varying dissolve rates based on different wall thicknesses so that a time-controlled release of the material can be provided.

A better understanding of the features and advantages of the present invention will be obtained by reference to the following detailed description and accompanying drawings which set forth an illustrative embodiment in which the principles of the invention are utilized.

BRIEF DESCRIPTION OF THE DRAWINGS

FIG. 1a is a top plan view of one embodiment of a tongue cleaning device.

FIG. 1b is a side plan view of the device of FIG. 1a.

FIG. 1c is a bottom plan view of the device of FIG. 1a.

DETAILED DESCRIPTION

The present disclosure describes a device that is suitable for oral use to clean and disinfect portions of the oral cavity. In particular, surfaces of the device can be augmented to add a variety of features that provide oral care benefits for cleaning and/or disinfecting the tongue and mouth. For example, as described herein, depressions may be formed in the surface to provide "suction cups" that help the device adhere to the roof of the mouth. Further, "blisters" may be formed in the surface to provide a deliverable material, such as mouthwash or medicine, to the mouth cavity. Advantageously, the blisters can be designed to dissolve at different rates, thus providing a timed-release control mechanism. However, it should be recognized that these and other features could have many shapes and sizes, and could be combined to suit particular applications. Thus, the embodiments described herein are merely illustrative and not limiting.

Figure 2:
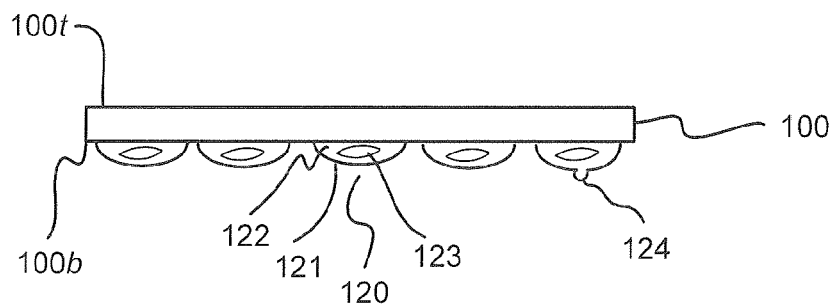
FIG. 2 is a side plan view of another embodiment of a tongue cleaning device.
Figure 3:
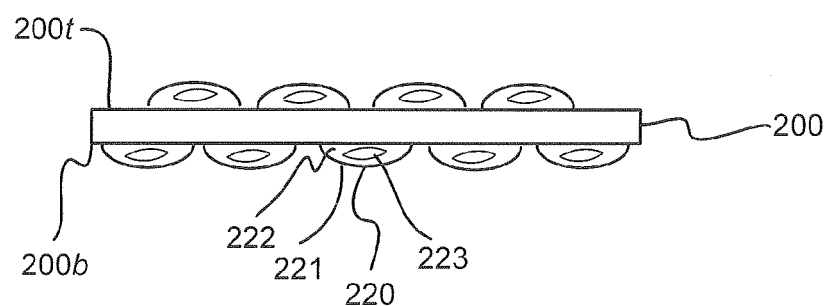
FIG. 3 is a side plan view of yet another embodiment of a tongue cleaning device.

FIGS. 1-3 show an oval-shaped device 8 having a main body 10 formed of a based material, preferably a soft, edible confection, such as used in GUMMI-BEAR or GUMMI-WORM type confections. Other materials could also be used, including gelatinous or gum-based materials, such as sodium alginate. Further, additional materials could be added to the base material to provide additional benefits. For example, a dentifrice could be added to the base material to provide a tooth cleaning polish that can act while the user chews or sucks on the device. The preferred overall length L of the device is approximately 1 inch to 1¾ inch, while the preferred overall the width W is approximately ¾ inch to 1 inch. The preferred thickness T of the device 10 is approximately ⅛ inch to ⅜ inch.

The top surface 10t of device 10 is generally smooth, but small circular depressions 12 (resembling suction cups) are formed in the surface. In a preferred embodiment, each depression measures approximately ⅛ inch to ⅜ inch in diameter and 1/64 inch to 1/32 inch deep. The depressions 12 assist the device in adhering firmly to the roof and soft palate of the mouth by a suction effect while the tongue moves across the bottom side 10b of the device. The suction cup depressions 12 may be formed in any type of pattern or randomly across the top surface 10t of the device.

The bottom surface 10b of device 10 is imbedded with hard segments 30 and at least one generally circular blister 20. Each of the hard segments 30 is preferably a hard dissolvable confection, such as hard peppermint candy, which can be formed using conventional confectionery methods to define a pattern, such as by extruding, molding or stamping. For example, in this embodiment, each segment 30 is approximately ⅛ inch to ⅜ inches long and ⅛ inches wide with raised scraping ridges 40, and forms a five-point star pattern defined by ridges 40 which extend from the surface 10b of the soft candy body by approximately 1/16 inch. The ridges 40 provide a rigid scraping surface that abrades the tongue as it passes along the device, which is adhered to the roof of the mouth. Other patterns with more ridges may prove equally effective.

The blister 20 is formed using conventional confectionary techniques to have a wall 21 that encloses a cavity 22. The cavity 22 is filled with a liquid, solid, or semi-solid material 23, such as a freshening and/or disinfecting agent, for example, mouthwash, which is released onto the tongue as the wall dissolves.

In use, the device 10 may be repeatedly removed and reapplied to different positions in the mouth. By moving the position of the device in the mouth, a more thorough coverage of the tongue by the abrasive scraping action of the device is provided. Such action may be repeated until the confection is fully dissolved.

In another embodiment, shown in FIG. 2, device 100 includes multiple blisters 120 formed on the bottom face 100b of the device, but no hard segments. Enclosed within each of the blisters 120 is a deliverable material 123, which is delivered onto the user's tongue as the walls 121 of the blisters dissolve. For example, pharmaceutical compositions, including antibiotics, disinfectants, and freshening agents, could be enclosed within the blisters 120 to treat the mouth in general, or targeted to treat specific portions of the mouth, such as the soft palette, tongue or cheeks. As another example, pieces of hard peppermint candy or similar could be provided, loose or attached, within at least some of the blisters 120. Further, a dentifrice could be provided within the blisters to provide a tooth polishing feature.

The walls 121 of blisters 120 could be formed with different thicknesses on the same device 100 in order to provide a time release control for delivery of material 123. Likewise, different devices could be specified for particular applications, with blisters and walls sized varying according to need. A device could be designed having blisters with suitable wall thicknesses to discharge a sore throat medication at intervals of three, five and ten minutes. Another device could be designed having blisters with suitable wall thicknesses to continuously discharge a medication for treating oral yeast infection for thirty seconds or longer. In one embodiment, a small nipple 124 could be formed in the center of a blister 120 that, when dissolved, allows a slow continuous flow of liquid from the blister. For example, chlorohexadine is an effective medication for treating infection, but is quickly dissolved in saliva thereby limiting its effectiveness for oral use. By providing a device with blisters designed for timed or continuous release control, chlorohexadine can be used more effectively for oral treatments.

In yet another embodiment, shown in FIG. 3, device 200 includes multiple blisters 220 formed on both the top face 200t and the bottom face 200b of the device. Enclosed within each of the blisters 220 is a deliverable material 223, which is delivered to the user as the walls 221 of the blister dissolve. As can be appreciated, many types of devices can be specified to deliver a particular material, where suction cups and blisters can be formed in a variety of configurations.

Although the subject matter has been described in language specific to structures and/or methods, it should be understood that the subject matter defined in the appended claims is not necessarily limited to the specific structures or methods described above. Rather, the specific structures or methods described above are disclosed as example forms of implementing the claims. For example, dimensions and materials are specified for the described embodiments, but many variations will be obvious to one with skill in such matters.

I claim:

1. A tongue cleaning apparatus, comprising a soft edible base material having at least one oral care surface feature comprising a dissolvable blister formed on a surface of the base material.

2. The tongue cleaning apparatus of claim 1, further comprising a second surface feature adapted for adhering the apparatus to a portion of a mouth.

3. The tongue cleaning apparatus of claim 2, wherein the second surface feature is a plurality of depressions formed in a surface of the base material.

4. The tongue cleaning apparatus of claim 1, including a third surface feature comprising a plurality of hard candy elements formed to extend from the surface of the base material.

5. The tongue cleaning apparatus of claim 1, wherein a disinfectant is contained within the blister.

6. The tongue cleaning apparatus of claim 1, wherein a breath freshener is contained within the blister.

7. The tongue cleaning apparatus of claim 1, wherein a tooth polishing material is contained within the blister.

8. A tongue cleaning apparatus, comprising a base material having a plurality of hard candy segments extending therefrom and at least one blister formed on a first surface thereof, wherein the blister is dissolvable and contains a deliverable material.

9. The tongue cleaning of claim 8, wherein the deliverable material is selected from a group consisting of antibiotics, disinfectants, freshening agents, and dentifrice.

10. A tongue cleaning apparatus as in claim 8, wherein the blister contains a liquid freshening agent.

11. A tongue cleaning apparatus, comprising:
a base material; and
a plurality of blisters formed on the surface of the base material, wherein each blister is dissolvable and contains a deliverable material.

12. The tongue cleaning apparatus of claim 11, wherein the deliverable material is selected from a group consisting of antibiotics, disinfectants, freshening agents, and dentifrice.

13. The tongue cleaning apparatus of claim 11, wherein the deliverable material is a plurality of hard candy segments.

14. The tongue cleaning apparatus of claim 11, wherein the base material is formed of a soft confection.

15. The tongue cleaning apparatus of claim 14, wherein the base material includes a dentifrice.

16. The tongue cleaning apparatus of claim 11, further comprising a plurality of depressions formed on a surface of the base material.

17. The tongue cleaning apparatus of claim 1, further comprising a plurality of dissolvable blisters formed on the surface of the base material, wherein at least some of the blisters are formed to have different dissolve rates.

18. The tongue cleaning apparatus of claim 17, wherein the blisters having different dissolve rates are formed to have different wall thicknesses.

19. The tongue cleaning apparatus of claim 1, wherein the base material includes a dentifrice.

20. The tongue cleaning apparatus of claim 1, wherein a medication is contained within the blister.

* * * * *